Figure 1A:
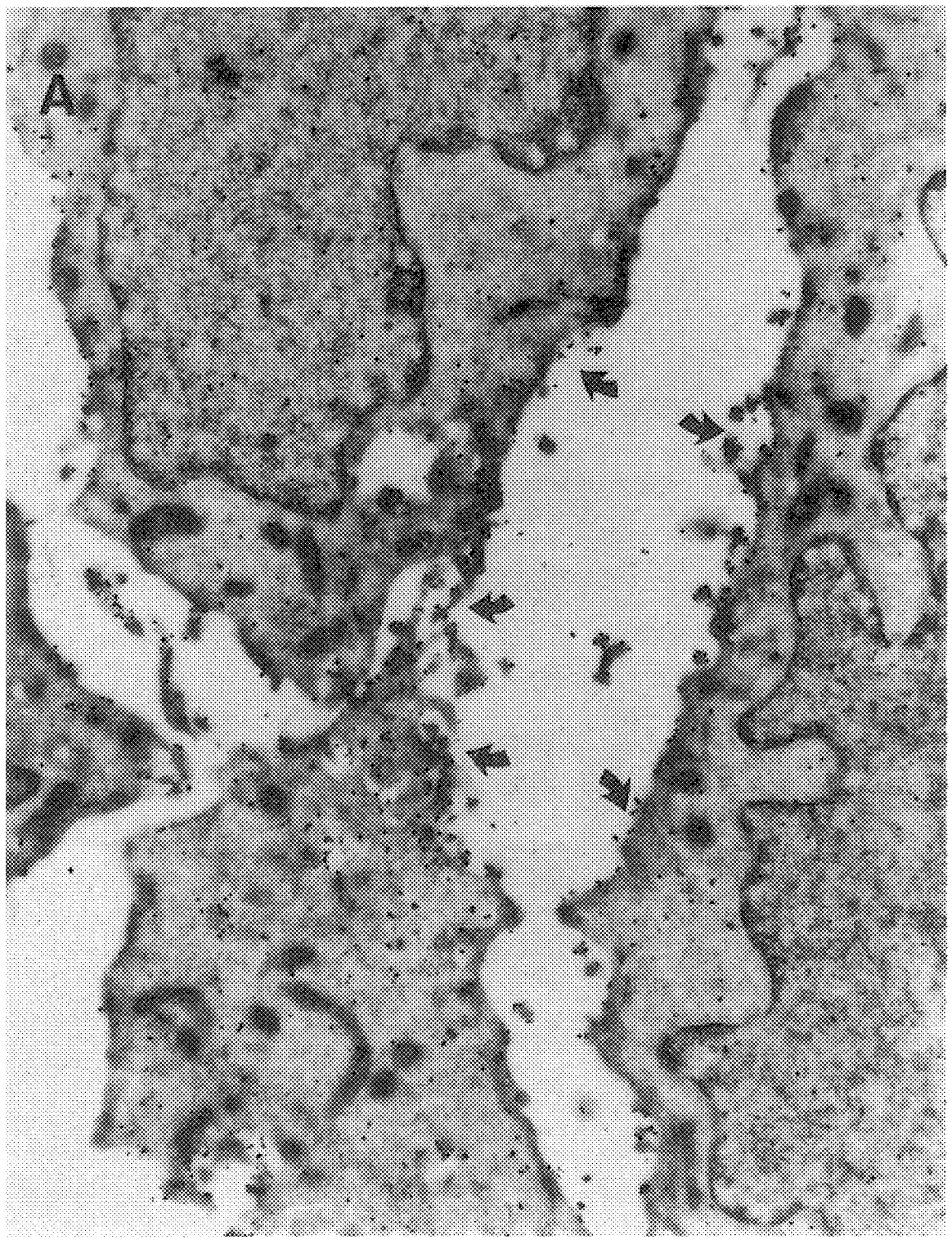

United States Patent [19]

Multhoff

[11] Patent Number: 5,932,478

[45] Date of Patent: Aug. 3, 1999

[54] HUMAN COLON CARCINOMA CELL LINES SHOWING STABLE HSP72 EXPRESSION

[75] Inventor: Gabriele Multhoff, München, Germany

[73] Assignee: GSF Forschungszentrum fur Unwelt und Gesundheit GmbH, Oberschleissheim, Germany

[21] Appl. No.: 08/970,699

[22] Filed: Nov. 14, 1997

[30] Foreign Application Priority Data

Nov. 15, 1996 [DE] Germany .......................... 196 47 426

[51] Int. Cl.$^6$ .................................................. C12N 5/10
[52] U.S. Cl. .......................................................... 435/371
[58] Field of Search ............................. 514/44; 435/371

[56] References Cited

PUBLICATIONS

Parham et al., "Monoclonal Antibodies: Purification, Fragmentation and Application to Structural and Functional Studies of Class I MHC Antigens", *Journal of Immunological Methods*, 53 (1982), Elsevier Biomedical Press, pp. 133–173.

Gomez et al., "An 80–Kilodalton Antigen from *Histoplasma capsulatum* That Has Homology to Heat Shock Protein 70 Induces Cell–Mediated Immune Responses and Protection in Mice", *Infection and Immunity*, American Society for Microbiology, Jul. 1992, pp. 2565–2571.

Danscher, "Localization of Gold in Biological Tissue–A Photochemical Method for Light and Electronmicroscopy", *Histochemistry*, (1981), Springer–Verlag, pp. 81–88.

Craig et al., "Heat Shock Proteins: Molecular Chaperones of Protein Biogenesis", *Microbiological Reviews*, American Society for Microbiology, vol. 57, No. 2, Jun. 1993, pp. 402–414.

Towbin et al., "Electrophoretic transfer of proteins from polyacrylamide gels to nitrocellulose sheets: Procedure and some applications", *Proc. National Academy of Science USA*, vol. 76, No. 9, Sep. 1979, pp. 4350–4354.

Laemmli, "Cleavage of Structural Proteins during the Assembly of the Head of Bacteriophage T4", *Nature*, vol. 227, Aug. 15,1970, pp. 680–685.

Multhoff et al., A Stress–Inducible 72–kDa Heat–Shock Protein (HSP72) Is Expressed On The Surface Of Human Tumor Cells, But Not On Normal Cells, *Int. J. Cancer*, 61, (1995), pp. 272–279.

Ferrarini et al., "Unusual Expression And Localization Of Heat–Shock Proteins In Human Tumor Cells", *Int. J. Cancer*, 51, (1992), pp. 613–619.

Srivastava, "Heat shock proteins in immune response to cancer: The Fourth Paradigm", *Experientia* 50, (1994), Birkhauser Verlag, pp. 1054–1060.

Jacquier–Sarlin et al., "Protective effects of hsp70 in inflammation", *Experientia* 50, (1994), Birkhauser Verlag, pp. 1031–1038.

Polla et al., "Spontaneous heat shock protein synthesis by alveolar macrophages in interstitial lung disease associated with phagocytosis of eosinophils", *European Respiratory Journal*, 6, 1993, pp. 483–488.

Welch et al., "Nuclear and Nucleolar Localization of the 72,000–dalton Heat Shock Protein in Heat–shocked Mammalian Cells", *The Journal of Biological Chemistry*, vol. 259, No. 7, Issue of Apr. 10, 1984, pp. 4501–4513.

Welch, "Mammalian Stress Response: Cell Physiology, Structure/Function of Stress Proteins, and Implications for Medicine and Disease", *Physiological Reviews*, vol. 72, No. 4, Oct. 1992, pp. 1063–1081.

Ullrich et al., "A mouse tumor–specific transplantataion antigen is a heat shock–related protein", *Proc. National Academy of Science USA*, vol. 83, May 1986, pp. 3121–3125.

Heufelder et al., "Cell Surface Localization of a 72 Kilodalton Heat Shock Protein in Retroocular Fibroblasts from Patients with Graves' Ophthalmopathy", *Journal of Clinical Endocrinology and Metabolism*, vol. 74, No. 4, 1992, pp. 732–736.

*Primary Examiner*—James Ketter
*Attorney, Agent, or Firm*—Greer, Burns & Crain, Ltd.

[57] ABSTRACT

The invention describes human colon carcinoma cell lines showing a stable expression of HSP72 of >80% or <20% and an essentially identical cell surface protein expression pattern of MHC and cell adhesion molecules.

12 Claims, 10 Drawing Sheets

SELECTED PREFERENCES: Arithmetic/Linear        Fig.6A

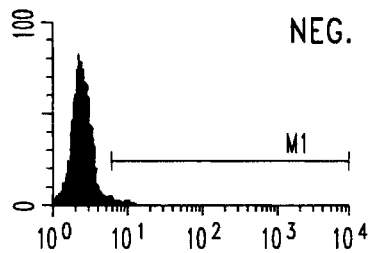

U3: 151.005\FL1-H\FL1-Height/FITC
--- Arithmetic Histogram Statistics for U3: 151.005 ---
Selected Preferences: Arithmetic/Linear
Parameter FL1-H FL1-Height/FITC    Gate G1= R1

| M | Left, | Right | Events | % | Peak | PkChl | Mean | Median |
|---|---|---|---|---|---|---|---|---|
| 0 | 1.00, | 9646 | 2725 | 100.00 | 146 | 2.21 | 2.55 | 2.37 |
| 1 | 5.83, | 9646 | 39 | 1.43 | 6 | 6.98 | 8.00 | 6.98 |

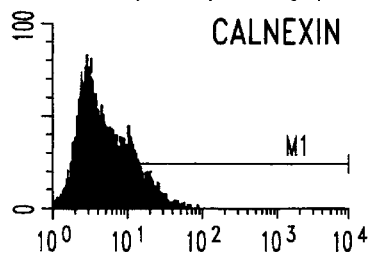

U3: 151.006\FL1-H\FL1-Height/FITC
--- Arithmetic Histogram Statistics for U3: 151.006 ---
Selected Preferences: Arithmetic/Linear
Parameter FL1-H FL1-Height/FITC    Gate G1= R1

| M | Left, | Right | Events | % | Peak | PkChl | Mean | Median |
|---|---|---|---|---|---|---|---|---|
| 0 | 1.00, | 9646 | 2760 | 100.00 | 75 | 2.64 | 6.33 | 3.92 |
| 1 | 5.83, | 9646 | 969 | 35.11 | 40 | 10.00 | 12.40 | 10.00 |

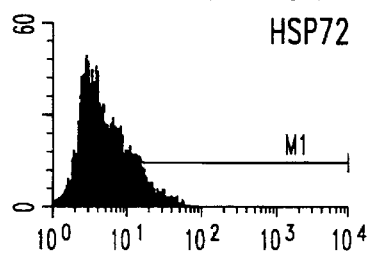

U3: 151.007\FL1-H\FL1-Height/FITC
--- Arithmetic Histogram Statistics for U3: 151.007 ---
Selected Preferences: Arithmetic/Linear
Parameter FL1-H FL1-Height/FITC    Gate G1= R1

| M | Left, | Right | Events | % | Peak | PkChl | Mean | Median |
|---|---|---|---|---|---|---|---|---|
| 0 | 1.00, | 9646 | 2663 | 100.00 | 75 | 2.46 | 5.79 | 3.65 |
| 1 | 5.42, | 9646 | 930 | 34.92 | 44 | 5.83 | 11.09 | 8.98 |

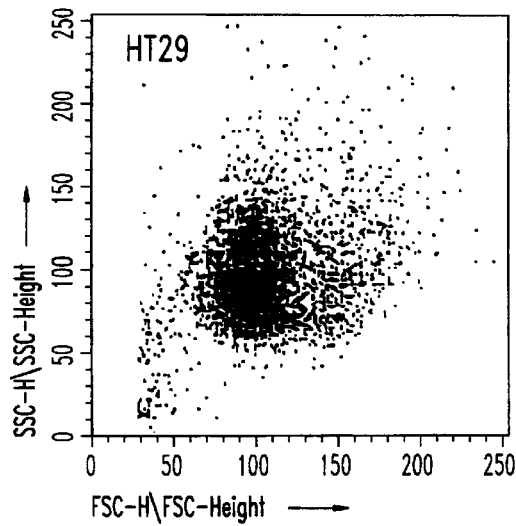

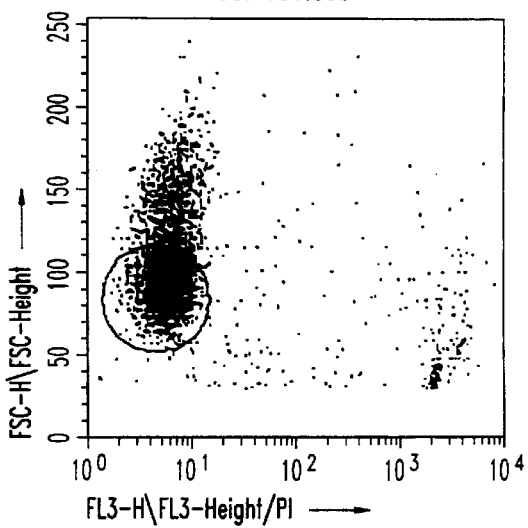

SELECTED PREFERENCES: Arithmetic/Linear        Fig.6B

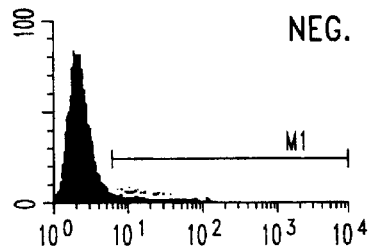

```
U3: 151.001\FL1-H\FL1-Height/FITC
--- Arithmetic Histogram Statistics for U3: 151.001 ---
Selected Preferences: Arithmetic/Linear
Parameter FL1-H  FL1-Height/FITC    Gate G1= R1
M  Left, Right   Events    %    Peak  PkChl  Mean  Median
0  1.00,  9646   2775   100.00   140   2.21   2.90   2.37
1  5.83,  9646     35     1.98     9   5.03  21.18   6.98
```

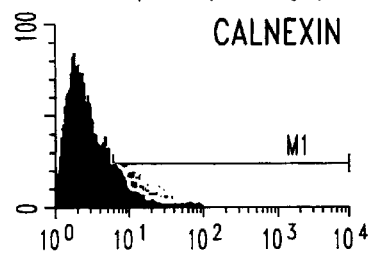

```
U3: 151.003\FL1-H\FL1-Height/FITC
--- Arithmetic Histogram Statistics for U3: 151.003 ---
Selected Preferences: Arithmetic/Linear
Parameter FL1-H  FL1-Height/FITC    Gate G1= R1
M  Left, Right   Events    %    Peak  PkChl  Mean  Median
0  1.00,  9646   2781   100.00    90   1.84   3.37   2.37
1  5.83,  9646    348    12.51    22   6.04   9.74   8.06
```

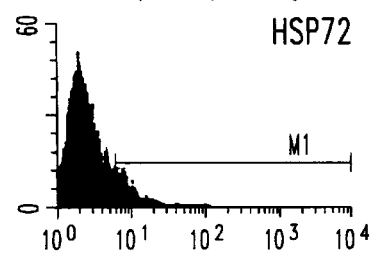

```
U3: 151.004\FL1-H\FL1-Height/FITC
--- Arithmetic Histogram Statistics for U3: 151.004 ---
Selected Preferences: Arithmetic/Linear
Parameter FL1-H  FL1-Height/FITC    Gate G1= R1
M  Left, Right   Events    %    Peak  PkChl  Mean  Median
0  1.00,  9646   2927   100.00    99   1.91   3.49   2.37
1  5.42,  9646    439    15.00    31   5.42   9.55   7.50
```

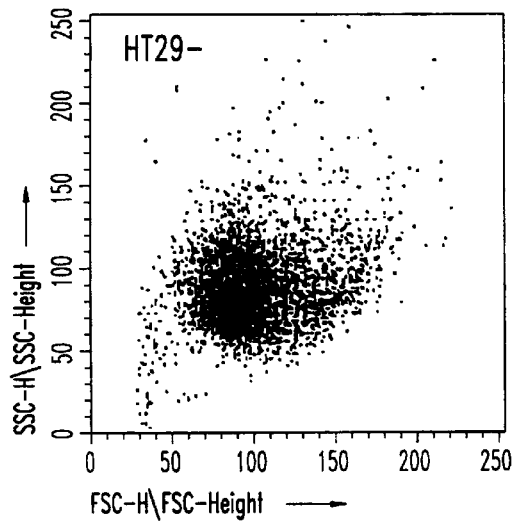

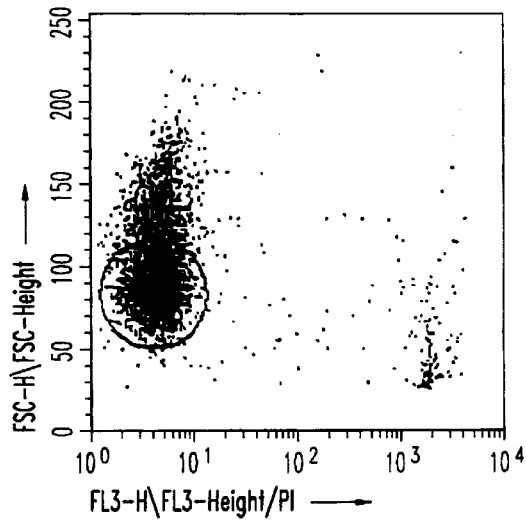

SELECTED PREFERENCES: Arithmetic/Linear

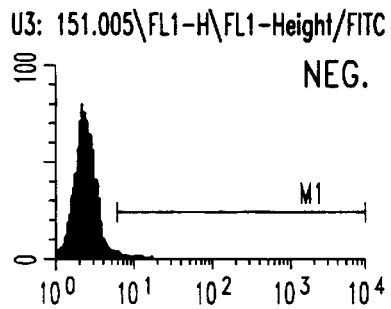

U3: 151.005\FL1-H\FL1-Height/FITC
--- Arithmetic Histogram Statistics for U3: 151.005 ---
Selected Preferences: Arithmetic/Linear
Parameter FL1-H FL1-Height/FITC   Gate G1= R1

| M | Left, | Right | Events | % | Peak | PkChl | Mean | Median |
|---|---|---|---|---|---|---|---|---|
| 0 | 1.00, | 9646 | 2725 | 100.00 | 146 | 2.21 | 2.55 | 2.37 |
| 1 | 5.83, | 9646 | 39 | 1.43 | 6 | 6.98 | 8.00 | 6.98 |

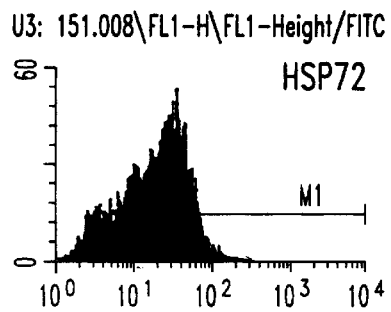

U3: 151.008\FL1-H\FL1-Height/FITC
--- Arithmetic Histogram Statistics for U3: 151.008 ---
Selected Preferences: Arithmetic/Linear
Parameter FL1-H FL1-Height/FITC   Gate G1= R1

| M | Left, | Right | Events | % | Peak | PkChl | Mean | Median |
|---|---|---|---|---|---|---|---|---|
| 0 | 1.00, | 9646 | 2315 | 100.00 | 53 | 40.68 | 20.46 | 23.71 |
| 1 | 5.42, | 9646 | 2017 | 87.13 | 53 | 40.68 | 32.15 | 27.38 |

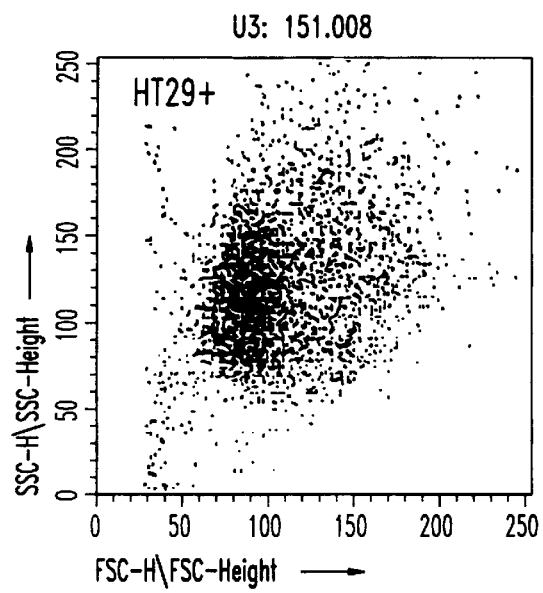

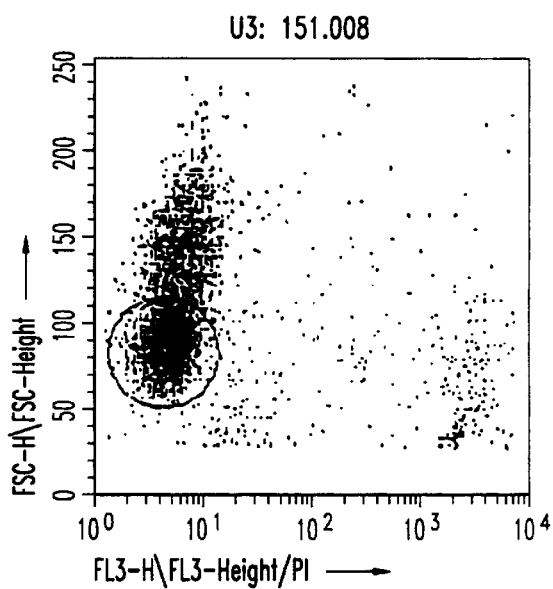

Fig.6C

HUMAN COLON CARCINOMA CELL LINES SHOWING STABLE HSP72 EXPRESSION

The invention relates to human colon carcinoma cell lines showing a stable expression of HSP72.

Molecular chaperones are necessary for a variety of fundamental processes and in particular function to fight cellular stress. The best studied class of chaperones is the group of heat shock proteins (HSP) having a molecular weight of 70 kDa. In the cell, they bind to and stabilize non-native conformations of other proteins, and, thus, inhibit the aggregation of unfolded proteins or enable their translocation across membranes (1, 2). It has been reported that HSP70 is localized in the cell nucleus (3), in the cytoplasm, and on the cellular surface of certain tumor cells (4, 5). Besides their function as chaperones in the cell the members of the HSP70 family seem to be involved in stimulation of the immune system, i.e. the pathology of several autoimmune diseases (6, 7), inflammatory processes associated with pathogens (8, 9), and in the cellular anti-tumor immune response in vivo and vitro (10).

The reasons for an immunodominance of highly conserved proteins such as heat shock proteins are still unknown. A review of the presently discussed hypotheses may be found (11).

Accessibility of HSP for immunocompetent effector cells seems to be a prerequisite for all immunostimulatory functions. Previous examinations showed that a heat-induced membrane expression of HSP72 on human sarcoma cells correlates with an increased sensitivity to lysis effected by natural killer cells (NK cells). The fact that HSP72 is expressed exclusively on the cellular surface of tumors but not on normal cells points to a function of HSP as a tumor-specific target structure for immunocompetent effector cells.

It is an object of the present invention to provide cell lines expressing HSP72 which allow for comparative examinations of for example the role of HSP72 in the immunogenicity of tumor cells.

This object has been achieved by the features characterized in more detail in claim 1. Preferred embodiments of the invention become obvious from the dependent claims.

Two preferred cell lines have been deposited at the DSMZ—Deutsche Sammlung Von Mikroorganismen Und Zellkulturon GmbH Mascheroder Weg 1b D-38124 Braunschweig, Germany on Oct. 29, 1996:

A human colon carcinoma cell line CX+ exhibiting a stable HSP72 expression at the cell surface of >80%, preferably >90%, accession number DSM ACC 2287. A human colon carcinoma cell line CX− exhibiting a stable HSP72 expression at the cell surface of <20%, preferably <10%, accession number DSM ACC 2288.

In the following, the invention will be explained in more detail with respect to colon carcinoma cell line CX2 as an example. However, the invention is not limited to this specific cell line. According to the invention, also other colon carcinoma cell lines may be used to achieve the object of the invention.

Any human colon carcinoma cell line may be used according to the invention which is known per se to the skilled artisan or which can easily be established by means of techniques known per se without requirement of an inventive step. The present invention as been carried out using two colon carcinoma cell lines, namely cell lines CX2 and HT29, as examples. The original cell line CX2 is available from the Deutsches Krebsforschungszentrum in Heidelberg. A tumor profile of this cell line including important genotypic parameters has been included. The same applies to cell line HT29. A deposition according to the Budapest treaty is not necessary since the invention can be repeatably imitated with respect to the literature presented. Furthermore, as mentioned above, any other human colon carcinoma cell line may be used to generate sublines with stable HSP72 expression of >80% or <20%, respectively, and an essentially identical cell surface protein expression pattern of MHC and cell adhesion molecules.

The invention will be detailed in the following regarding the accompanying Figures. The Figures show:

FIGS. 1A–1C.

Electron micrograph of a cryo-ultramicrotomic section of labeled HSP72 on the surface of CX2 human colon carcinoma cells. The frozen sections were treated with anti-HSP72 mab (RPN1197, Amersham), and subsequently labeled with silver-enhanced ultra-small gold. HSP72 labeling is not restricted to subcellular regions in the cytoplasm and nucleus; A and B show that HSP72 can also be detected on the plasma membrane. C represents a control labeling with silver enhancement and without primary antibody. The arrow indicates the accumulation of HSP72 on the plasma membrane projections; N indicates the nucleus (X 43,000).

FIG. 2:

SDS PAGE analysis of HSP72 immunoprecipitated from the cell surface of biotinylated CX2 tumor cells.

Lane A: rHSP70 protein (50 ng) detected by specific anti-HSP72 mab;

Lanes B and C: immunoprecipitations obtained with antiHSP72 (lane B) or anti-MHC class I mab (lane C) on 0.1% NP40 lysates after selective cell surface biotinylation.

On the left molecular weight standard.

On the right : arrows indicate a 72 kDa and a 45 kDa band, respectively.

FIG. 3:

Cell surface expression of HSP72 on CX2 colon carcinoma cells following cell sorting by flow cytometry using HSP72 specific mab. The results are presented logarithmically with the green fluorescence intensity plotted versus the cell number. The broken lines represent the negative control; the solid line represents anti-HSP72 mab.

FIG. 4:

HSP72 immunoblot of cytoplasmic lysates of CX+, CX2, and CX− carcinoma cells under physiological conditions (open bars) and after a mild heat shock at 41.8° C. for 2 hours and subsequent recovery phase at 37° C. for 2 hours (hatched bars). The amounts of HSP72 protein (marked by an arrow) were evaluated in relation to actin (designated by "a"). Identical amounts of protein (10 $\mu$g of cell lysates) were electrophoresed on a 10% SDS PAGE using reducing conditions and transferred to nitrocellulose. The 72 kDa protein band was visualized by HSP72-specific mab and detected with the ECL system. The immunoblots were quantified by laser densitometry. The results represent the mean value of at least two independent experiments.

Insert: A representative immunoblot.

The relative rate of HSP72 induction is indicated below each bar.

FIG. 5:

Example of HSP72 sorting together with the setting parameters.

FIGS. 6A–C:

Examples for cell sorting experiments (FACS-analyses) of HT29.

According to the invention, the original colon carcinoma cell line, Cx2, could be separated into a cell line expressing high amounts of HSP72 (CX+: expression >80%, in particular >90%), and into a cell line expressing low amounts of HSP72 (CX–: expression <20%, in particular <10%). These sublines were obtained by cell sorting via HSP72 expression at the cell surface using a suitable antibody. The human tumor cell lines available so far had the disadvantage that they failed to exhibit a stable expression of heat shock proteins over a longer period of time, i.e. after a certain time the HSP expression decreased and another heat shock was necessary to reinduce expression.

According to the invention, it has been demonstrated that human colon carcinoma cell lines after cell sorting of the original cell line by means of a monoclonal antibody directed against HSP72 are able to stably express HSP72 where, surprisingly, it has been possible to obtain cell lines by cell sorting which express HSP72 stably in an amount of >80% and in an amount of <20%, respectively.

This result was unexpected because the original cell line initially showed a stable HSP72 cell surface expression of >60% tested over more than 20 cell passages. This finding suggests that this expression rate of 60% was indispensable for survival, cell cycle, cell adhesion, etc.

Therefore, it could be expected after cell separation of CX2 cells into the HSP72 high-expressing subline and the HSP72 low-expressing subline that after a few cell passages both sublines would level out again at a HSP72 cell surface expression rate of approximately 60%. Surprisingly, this has not been the case. Both cell lines, CX+ and CX–, showed a stable expression pattern of HSP72 cell surface expression CX+>80%, CX–<20%.

Normally, such cell lines have a different expression pattern of cell surface proteins. According to the invention, it could be surprisingly demonstrated that cell lines obtained by cell sorting of human colon carcinoma cell lines have an identical cell surface protein expression pattern of MHC and cell adhesion molecules. For this purpose, the typical cell adhesion molecules ICAM (intercellular adhesion molecule), NCAM (nerve cell adhesion molecule), and VCAM (vascular cellular adhesion molecule), as well as MHC class I and class II were examined for expression.

Thus, the colon carcinoma cell lines of the invention differ only in their HSP72 cell surface expression pattern while they are identical in their expression pattern of MHC and cell adhesion molecules.

Since the cell lines CX+ and CX– provided exemplarily were derived from a defined homogenous original cell line (CX2) their HLA background (all HLA alleles) is identical; thus, they represent an autologous HLA tumor cell system.

Thus, cell lines have been provided according to the invention which are excellently useful to perform functional studies of heat shock proteins of the HSP70 family.

The human colon carcinoma cell sublines obtained by cell separation, for example CX+ and CX–, make it possible to study the importance of HSP (HLA independent) for the immunogenicity of tumor cells. Furthermore, the cell lines provided by the invention, for example CX+ and CX–, may be used as feeder cells for the cloning of NK cells and selection of suitable cells (NK clones with HSP72 specificity). These clones could be used to perform receptor analyses to find out about the existence of a HSP72-specific receptor on NK cells.

Figure 1B:
Figure 1C:
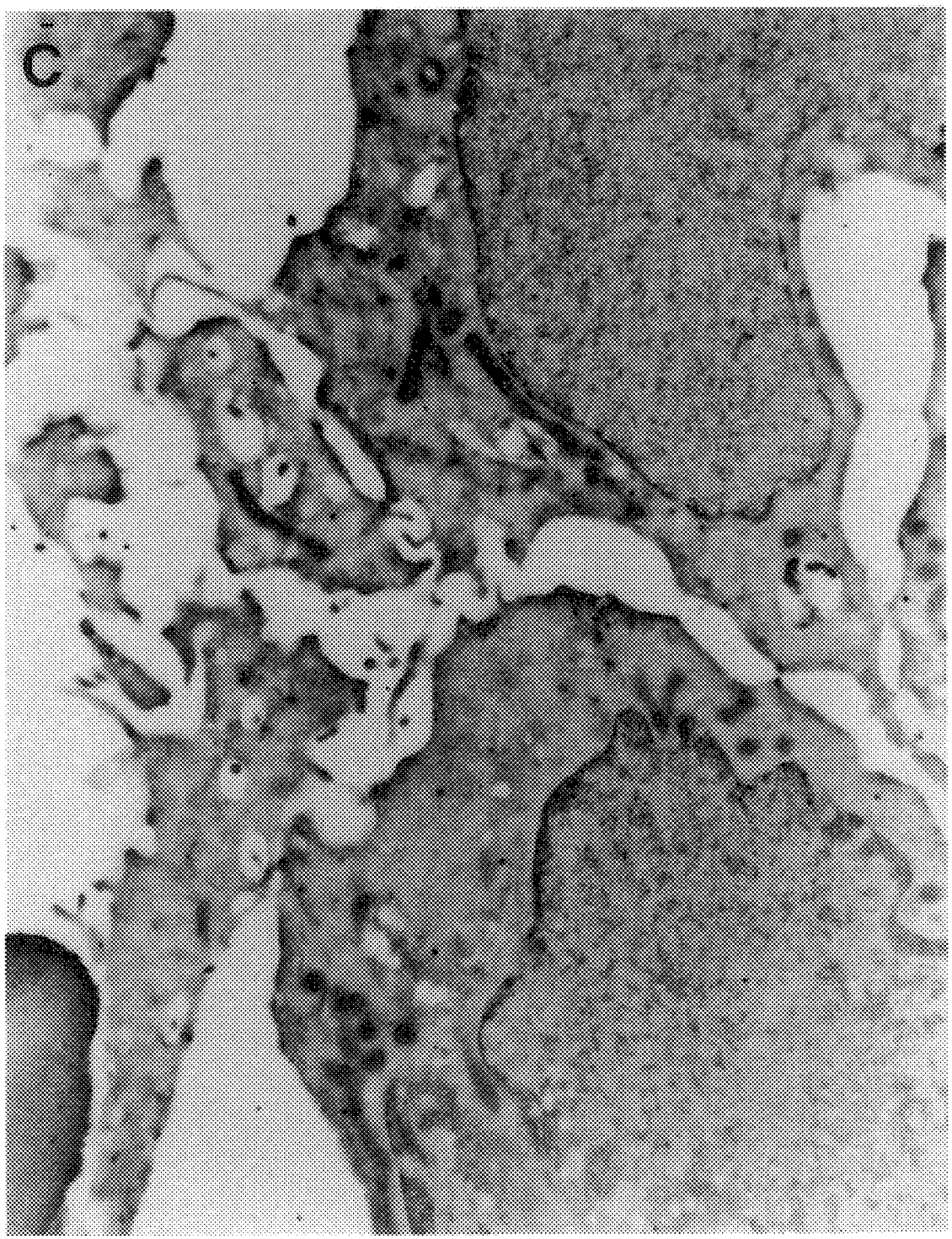

Thus, it could be demonstrated according to the invention that HSP72 is expressed on the cellular surface of colon carcinoma cells and that these cell lines may be splitted by cell sorting into stable sublines expressing HSP72 in an amount of >80% and <20%, respectively, over more than 20 cell passages. The expression at the cell surface and the subcellular localization of HSP72 were studied by electron-microscopy using ultra-small gold particles and silver staining. The immunoelectron micrograph of FIG. 1A demonstrates the association of HSP72 (black dots) with the plasma membrane of Cx2 colon carcinoma cells. Since the membrane was permeable before antibody incubation, HSP72 is also detectable in the cytoplasm and in the cell nucleus. The result of the distribution of HSP72 on a different section of two colon carcinoma cells is presented in FIG. 1B:

The cell in the upper part of the electron micrograph shows an enrichment of HSP72 molecules on the projections of the plasma membrane and in vesicular structures. FIG. 1C shows background staining of three colon carcinoma cell lines without incubation with the primary antibody.

Figure 2:
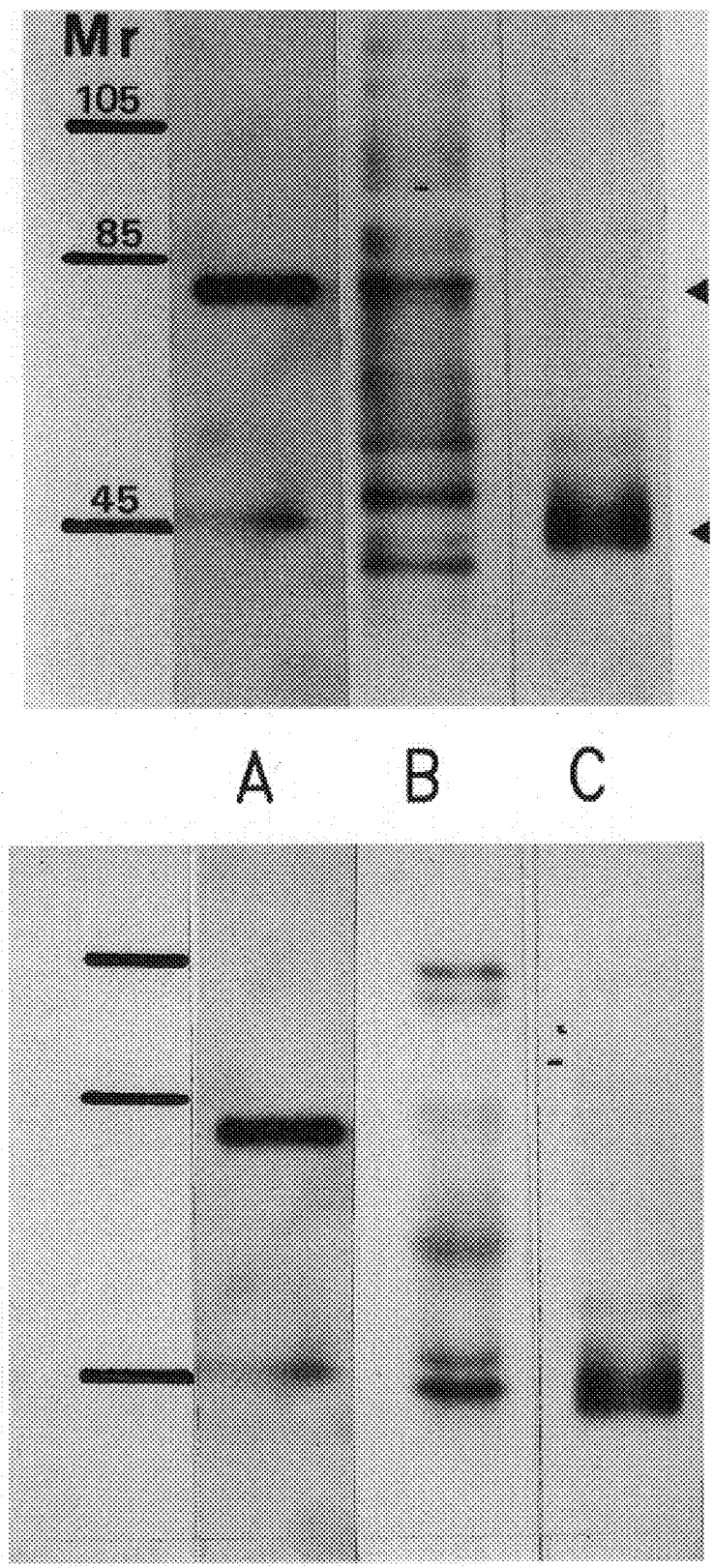
Figure 3:
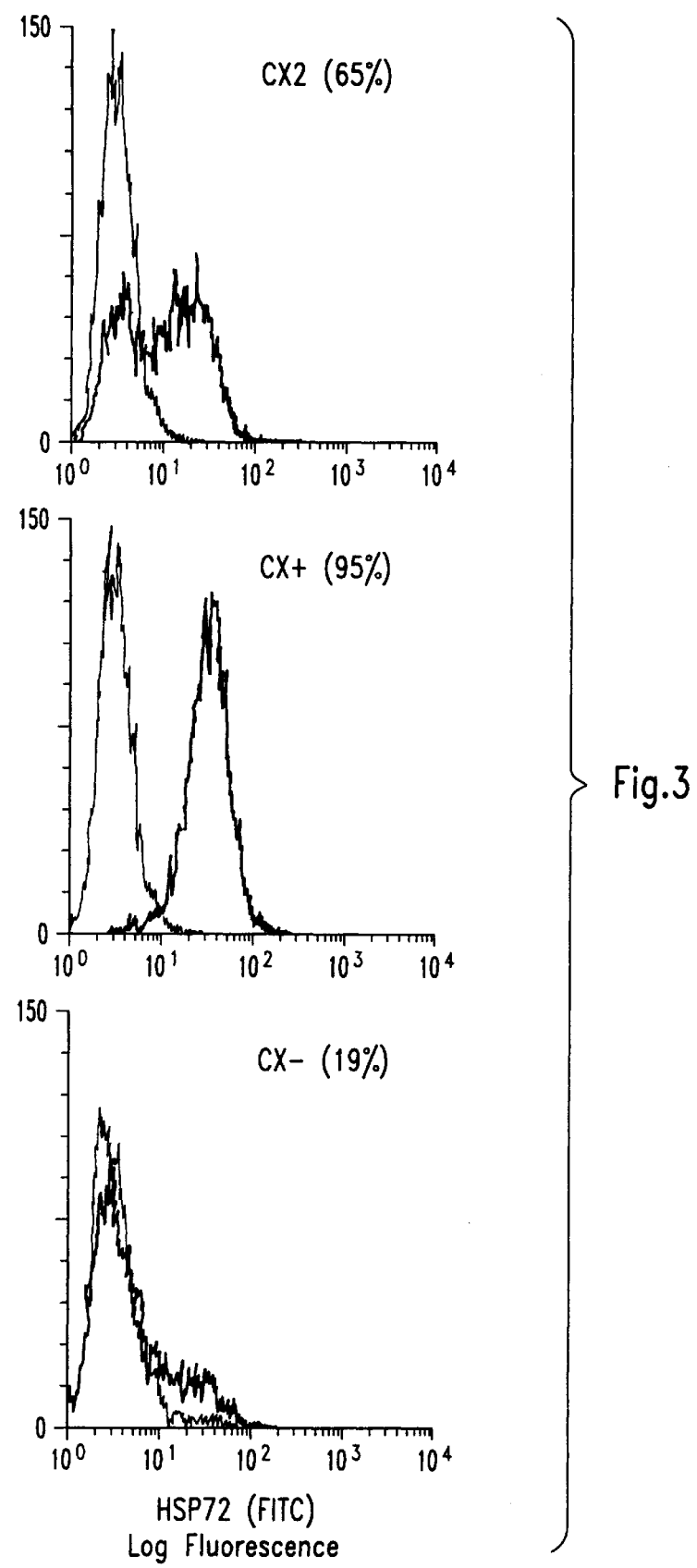

Furthermore, the cell surface expression of HSP72 on CX2 tumor cells was shown by selective cell surface biotinylation. A comparison of the biotinylated cell surface expressed HSP72 with recombinant HSP70 (FIG. 2, lane A) shows that an intact HSP72 molecule can be immunoprecipitated from the cell surface of CX2 cells (FIG. 2, lane B). FIG. 2, lane C shows a 45 kDa band representing MHC class I molecules immunoprecipitated by mab W6/32. Quantification of the HSP72 cell surface expression on CX2 cells was performed by indirect immunofluorescence studies using HSP72-specific mabs RPN1197 and 3A3 followed by FACScan analysis. Under physiological conditions, the HSP72 molecules were constantly expressed on about 60% of cells (cf. FIG. 3).

Figure 4:
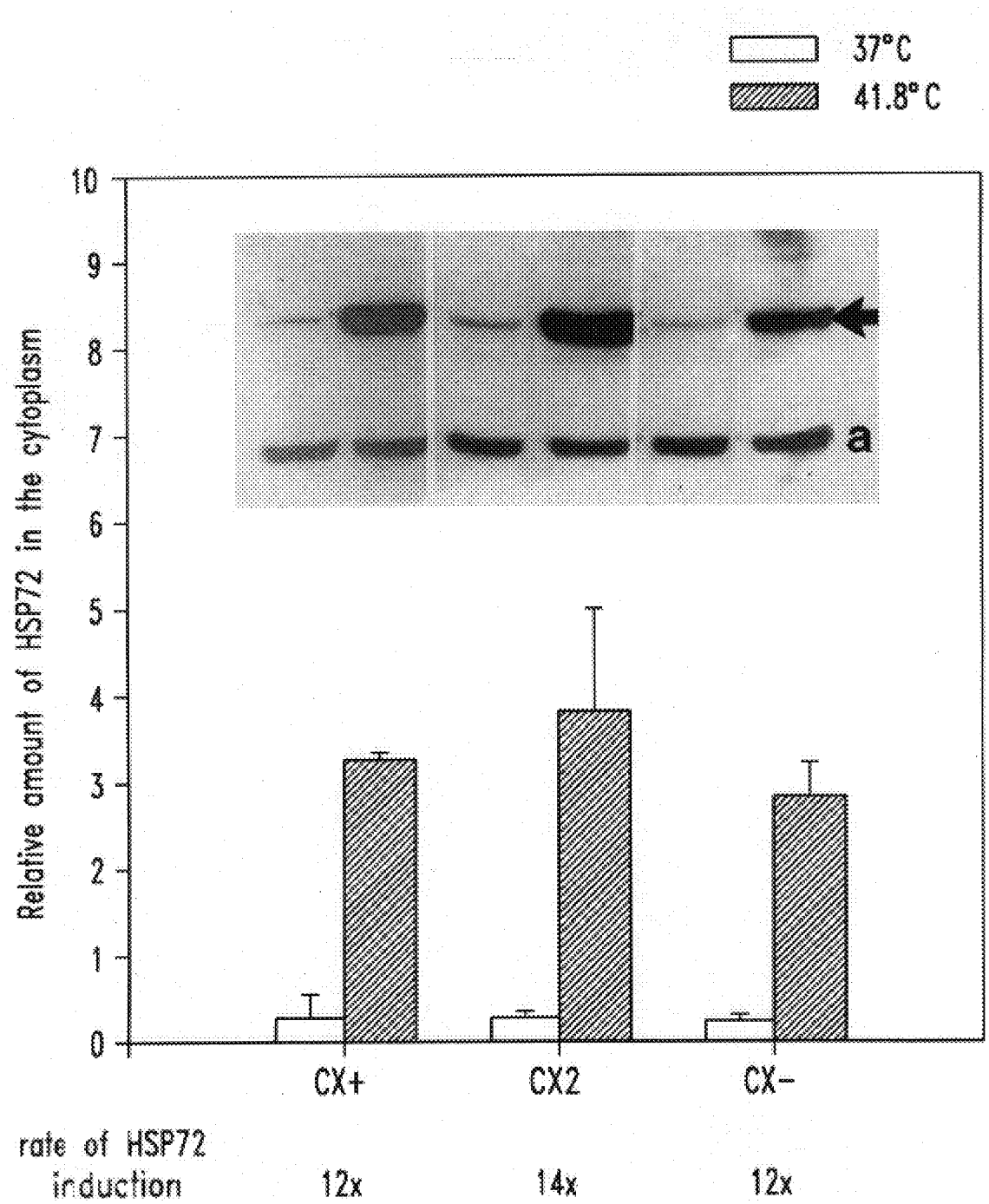

According to the invention, the CX2 colon carcinoma cell line was splitted by cell sorting as described in Materials and Methods into a subline expressing more than 80%, preferably more than 90% of HSP72, and into a subline expressing less than 20%, preferably less than 10% of HSP72. Representative histograms of the phenotypic characterization of HSP72 cell surface expression on CX2, CX+, and CX– cell lines are presented in FIG. 4. It could be demonstrated by comparative flow cytometric analysis of the expression of MHC, adhesion molecules, and HSP that the CX2 original cell line, and the Cx+ and CX– sublines differ only in their capability to express HSP72 but not in the other cell surface markers studied (cf. Table 1). At comparable cell densities, the CX2, CX+, and CX– cells exhibited comparable ICAM-1 expression. This cell surface expression pattern remained stable for more than 30 cell passages.

Figure 5:
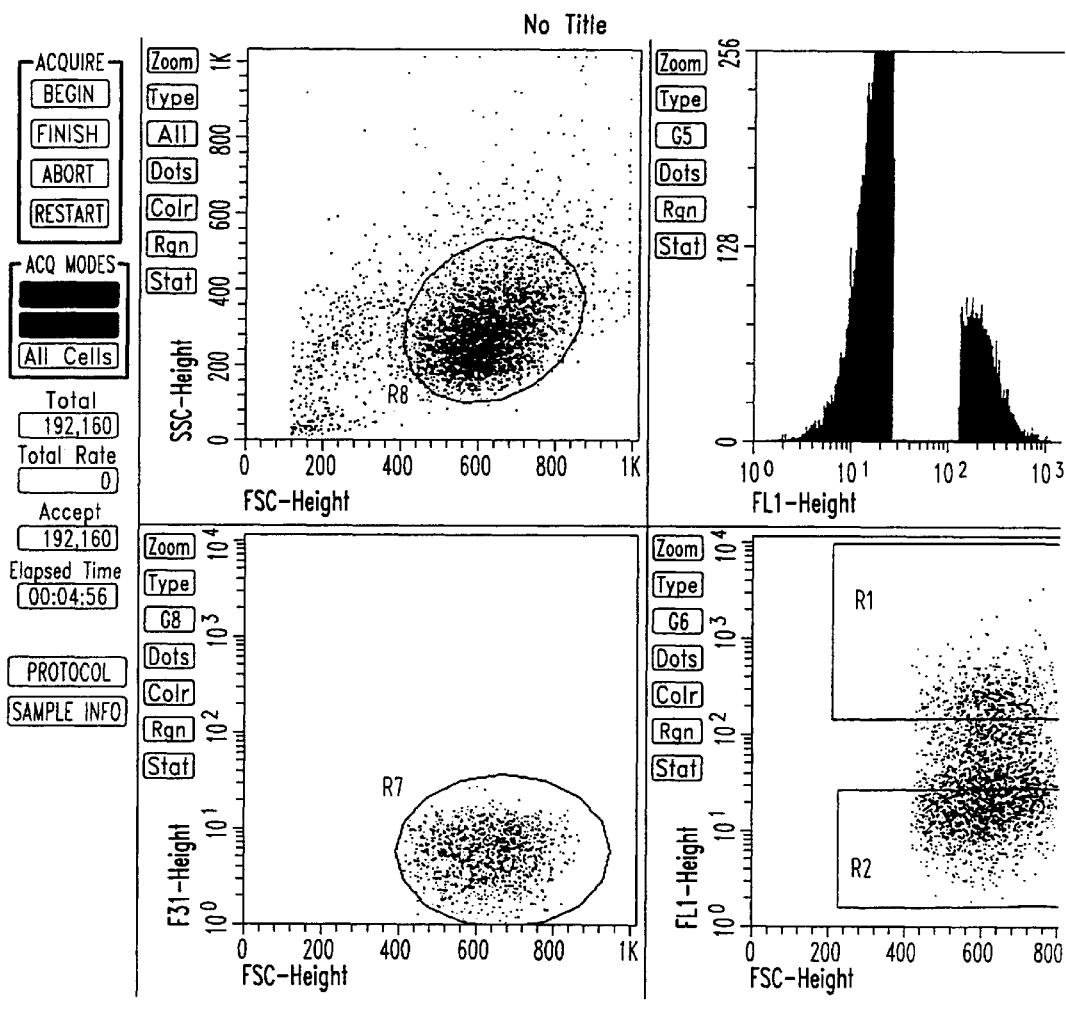

In contrast to the profound differences in the level of HSP72 cell surface expression, it was shown by flow cytometry and electron microscopy that the cytoplasmic amount of HSP72 in the original CX2 cell line and in the CX+ and CX– sublines was comparable under physiological conditions and after a mild heat treatment (41.8° C., 2 hours). As shown in FIG. 5 a mild heat shock in all three cell lines results in a comparable HSP72 induction (about 13-fold).

Thus, it was surprisingly shown according to the invention that already under physiological conditions human colon carcinoma cell lines reveal a cell surface expression of HSP72 of approximately 60% of cells. This unexpected expression of HSP72 on the cell surface of colon carcinoma cells formed the basis of the splitting performed according to the invention into two CX2 colon carcinoma sublines expressing HSP72 to at least more than 80% (CX+) and less than 20% (CX–) of the cells. The separation into sublines was effected via the expression of HSP72 on the cell surface of the colon carcinoma cell lines by cell sorting using suitable antibodies. The flow cytometric analysis performed revealed that surprisingly the cell surface expression pattern of HSP72 on the original CX2 cell line and in both of the CX+ and Cx– sublines remained stable for more than 30 cell passages. Furthermore, the surface expression pattern was not affected by heat stress. Despite these clear differences in HSP72 expression the cells at comparable cell densities exhibited a comparable and constant expression pattern of MHC and adhesion molecules.

Thus, the "Tautologous" tumor cell system provided by the invention differs only in the expression of one antigen (HSP72) while the expression of MHC and cell adhesion molecules is identical.

No differences were observed on the cytoplasmic level regarding the expression rate and the amount of HSP72 expressed. After heat exposure it was possible to equally induce the expression of HSP72 in the cytoplasm of both cell lines. Also regarding growth parameters and morphology of the cell lines no significant differences were observed. The doubling time is about 25 hours in both of the cell lines. Viability is comparable for both cell lines. Also, a comparable thermotolerance has been observed against temperatures ranging from 40° C.–44° C.

Thus, the invention has provided for the first time a system useful to study the role of HSP72 as tumor-specific target structure in an autologous tumor cell system.

Further, it could be demonstrated that the heat-independent expression of HSP72 on the surface of CX2 and CX+ colon carcinoma cells is in close correlation to the sensitivity of these cells for lysis by NK cells. This indicates that no other heat-inducible factor besides HSP72 is necessary for recognition by NK cells.

HSP72 has a total length of about 700 amino acids. The N terminus consists of amino acids 1–450, the C terminus of amino acids 450–650 (cf. FIG. 6). The amino acid sequence of HSP72 is known per se and is published for example in Hunt & Morimoto, Proc. Natl. Acad. Sci. USA 82 (1985), 6455–6459.

Further, according to the invention there was studied the role of differential expression of the HSP72 cell surface protein in this "Tautologous" colon carcinoma cell system with respect to its sensitivity against NK cell-mediated lysis. It could be demonstrated that lysis by NK cells was increased in the HSP72 high-expressing CX+ subline by more than twofold as compared to the HSP72 low-expressing CX− subline. Lysis sensitivity of the original CX2 tumor cell line was approximately in between that of the CX+ and CX− cells.

Moreover, it could be shown that a heat shock neither functions to bring about an increased HSP72 cell surface expression nor an increased sensitivity to lysis by NK cells.

By antibody blocking assays the NK cell-mediated lysis sensitivity could be correlated to the amount of HSP72 expressed on the cell surface. Using the HSP72-specific monoclonal antibody, the strongest inhibition was found with CX+ cells, a median lysis inhibition with the original CX2 tumor cell line and no lysis inhibition with the CX− cell subline. A control antibody of the IgGi isotype and a MHC class I-specific antibody had no inhibitory effect on the lysis pattern of any of the three tumor cell lines mentioned, CX2, CX+, and CX−.

As already detailed above, the "autologous" tumor cell system differs only with regard to the expressing of a single antigen, thereby enabling the examination of the role of NSP72 as a tumour specific target structure according to the invention. It has been demonstrated in the literature (16) that member of the HSP70 family cause a cellular immune reaction in vivo as well as in vitro. For this reason, we compared the lysis sensitivity of the "autologous" colon carcinoma sublines of the invention which differ only in HSP72 expression on the cell surface. To carry out cytotoxicity assays in these colon carcinoma sublines an effector cell population was used which was supplemented with NK. The heat-independent cell surface expression of HSP72 on CX2 and CX+ colon carcinoma cells closely correlated with NK cell-mediated lysis sensitivity. These data show that no additional heat-inducible factor besides HSP72 is required for the NK cell-mediated recognition mechanism.

Thus, the expression of HSP72 is an additional factor determining the sensitivity of tumour target cells towards NK cell-mediated lysis. Therefore, the expression of HSP72 may be used in tumour therapy to stimulate NK cells.

TABLE 1

A comparative flow cytometric analysis of the cell surface expression of MHC, adhesion molecules, and HSP72 on CX2, CX+, and Cx− carcinoma cells (n = 5).

|  | MHC I W6/32 | MHC II L243 | ICALM-I anti-CD54 | VCAM anti-CD106 | HNK1 anti-CD57 | NCAM anti-CD56 | HSP72 anti-HSP72 |
|---|---|---|---|---|---|---|---|
| CX2 | +++ | − | ++ | − | − | + | ++ |
|  | (99 ± 0.5) | (5 ± 3.7) | (58 ± 2.3) | (8 ± 0.5) | (7 ± 1.5) | (21 ± 4.6) | (66 ± 6.8) |
| CX+ | +++ | − | ++ | − | − | + | +++ |
|  | (99 ± 0.8) | (10 ± 0.5) | (68 ± 7.7) | (11 ± 3.5) | (12 ± 6.6) | (26 ± 2.3) | (93 ± 3.4) |
| CX− | +++ | − | ++ | − | − | + | − |
|  | (99 ± 0.5) | (10 ± 4.7) | (48 ± 4.5) | (12 ± 4.5) | (10 ± 4.0) | (24 ± 8.8) | (18 ± 6.0) |

+++: >90%
++: >50%
+: >20%
−: <20%

MATERIALS AND METHODS

CELL CULTURE

The human CX2 colon carcinoma cell line (tumor bank DKFZ Heidelberg) and the CX+ and CX− subclones were cultured in RPMI 1640 medium (Gibco, Eggenstein) supplemented with 10% heat-inactivated fetal calf serum (FCS, Gibco, Eggenstein) and antibiotics.

PREPARATION OF CX2 TUMOR CELLS FOR FACS SEPARATION:

First the cells to be analyzed were washed twice in cold PBS/10% FCS medium. The cellular pellet ($5 \times 10^6$ cells) was resuspended and incubated for 30 minutes on ice with 5 $\mu$l RPN1197 (anti-HSP72 mab; Amersham; code RPN 1197). To remove antibodies not bound to the cells after this incubation phase the cells were again washed twice with cold PBS/10% FCS medium. Thereafter, these cells were incubated with 5 $\mu$l of fluorescein isothiocyanate (FITC) conjugated rabbit anti-mouse antibody (DAKO; code No.

F0232) for 30 minutes in the dark on ice. Excess of FITC antibody was removed by washing the cells twice which then were resuspended in 2 ml cold PBS/10% FCS medium and stored on ice in the dark until separation. To distinguish between viable and dead cells 10 $\mu$l of propidium iodide (PI; 50 $\mu$g/ml) was added to the samples. Using a FACS Star sorter, the "original cell line" CX2 was separated by virtue of fluorescence labeling into two daughter lines: a CX− line expressing less than 20% of HSP72 on the cell surface, or a CX+ line expressing more than 80% of HSP72, respectively.

HEAT TREATMENT

Exponentially growing CX2 cells were treated for two hours at the non-lethal temperature of 41.8° C. in a temperature-controlled water bath (Haake E3, Karlsruhe), and were afterwards incubated for twelve hours at 37° C. The survival rate of the heat-treated cells was always greater than 95% as determined by trypan blue exclusion and PI staining.

MONOCLONAL ANTIBODIES (MAB), INDIRECT IMMUNOFLUORESCENCE AND FACSCAN ANALYSIS:

The following antibodies were used for phenotypic characterization of effector and tumor cells on a FACScan instrument (Becton Dickinson, Heidelberg), for cell sorting* on a FACS Stab Plus instrument ((Becton Dickinson, Heidelberg), for antibody blocking studies and immunoprecipitation* (methods as described below).

and 1D SDS PAGE: The antibody selectively detects HSP72 and shows no cross-reaction to HSP73. Cytoplasmic HSP70 expression was detectable by the following antibodies: RPN1197 (Amersham), 3A3 (S. Fox), C92F3A-5 (StressGen), and 5G10 (Pharmagen). Cell surface staining and cell sorting of the tumor cells was performed using mab RPN1197 (Amersham). After sorting, the HSP72 high-expressing (CX+) and low-expressing (CX−) sublines were cultured separately.

Cell sorting of effector cells was performed via CD3 and CD14. The negatively separated CD3 effector cell population was stimulated with 100 IU of rIL-2 and used for functional studies. Phenotypic characterization of these cells was carried out using CD3/CD16+56 and CD14/CD45 double-stained antibodies.

ELECTRON MICROSCOPY

PBS-washed CX2 tumor cells were fixed in 8% paraformaldehyde in HEPES (250 mM) buffer for 1 hour. After two washes free aldehyde groups were quenched in 50 mM $NH_4Cl$ for 10 minutes. For cryoprotection the cell pellets were stored suspended in a volume of 2.1 M sucrose in polyvinyl pyrrolidone (17%) at 20° C. for 30 minutes. Then, the cell pellets were frozen in liquid nitrogen, and ultra-thin sections (70 nm) were cut at −100° C. on an ultracut microtome (Reichert-Jung FC4E) using a glass knife and were mounted on 150 mesh parlodion-coated nickel grids. Immunogold labeling of HSP72 was carried out according to

| Antibody: | Specificity: | Isotype: | Source |
|---|---|---|---|
| control | isotype ctrl. | IgG2a | Dianova**, Hamburg, FRG |
| control | isotype ctrt. | IgG1 | Dianova |
| W6/32 | MHC class I | IgG2a | J. Johnson***·***, LMU Munich, FRG |
| L243 | HLA DR | IgG2a | J. Johnson |
| anti-CD54 | I-CAM | IgG1 | Dianova |
| anti-CD56 | N-CAM | IgG1 | Dianova |
| anti-CD16 | Fcy RIII | IgG1 | Dianova |
| anti-CD57 | HNKI | IgM | Dianova |
| VCAM-1 | V-CAM | IgG1 | Dianova |
| anti-CD3 | T | IgG1 | Dianova |
| QKT3 | T | IgG2a | ATCC* |
| anti-CD14 | monocytes | IgG2a | Dianova* |
| RPN1197 | H5P72 | IgG1 | Amershani, Braunschweig, FRG*··* |
| 3A3 | HSP72 | IgG1 | S. Fox, NW University, Illinois, USA |
| CD3/CD16 + 56 | T/NK | rgG1/IgG1 | Becton-Dickinson, Heidelberg, FRG |
| CD45/CD14 | lymph. | IgG1/IgG2b | Becton Dickinson |
| FITC rabbit anti-mouse | | Ig | Dako |

The flow cytometric studies were performed using exponentially growing cells and at comparable cell densities. Viable cells (1×10⁶) were incubated with either one of the antibodies shown above at a final concentration of 1–5 $\mu$g/0.5–1×10⁶ cells for 30 minutes at 4° C. The antibodies used for FACScan analysis and cell sorting contained 0.1% sodium azide; the antibodies for antibody blocking experiments were sodium azide-free. After incubation with the primary non-stained antibodies the cells were washed twice with PBS/10% FCS solution and incubated with a second fluorescein isothiocyanate (FITC) conjugated rabbit anti-mouse IgG antibody (FITC, DAKO, Hamburg) for another 30 minutes at 4° C. The percentage of positively stained cells was defined as the difference between the number of specifically stained cells minus the number of cells stained by isotype-matched control antibodies. The values obtained from the FACScan analysis represent mean values of at least four independent experiments.

The specificity of antibody RPN1197 (Amersham), an anti-HSP72 mab, which was used in the present experiments was demonstrated earlier (5) by Western blotting after 2D the method described by Danscher (12) using ultra-small gold samples and subsequent silver enhancement.

SELECTIVE CELL SURFACE BIOTINYLATION AND IMMUNOPRECIPITATION

For the detection of HSP72 cell surface expression viable cells (2×10⁷) were biotinylated with biotin ester (RPN2202, Amersham) for 30 minutes at 4° C. After washing the cells were lysed for 20 minutes in ice-cold lysis buffer (0.1% NP40; 250 mM NaCl; 25 mM Tris-HCl, pH 7.5; 5 mM EDTA, 2 $\mu$g/ml aprotinin, 10 $\mu$g/ml PMSF). The extracts were clarified by microcentrifugation for 15 minutes at 4° C. and immunoprecipitated with W6/32 mab (2 $\mu$g) and 50 $\mu$l gamma-bind plus protein G sepharose beads for 3 hours at 4° C. Afterwards the conjugated antigen-loaded sepharose beads were washed three times in ice-cold lysis buffer and resuspended in 75 $\mu$l of sample buffer (200 mM DTT; 20% glycerol; 0.12 M Tris; bromphenol blue). The proteins from the sepharose beads were separated on 10% SDS PAGE, blotted onto PVDF membrane and detected by ECL after incubation with peroxidase-conjugated anti-streptavidin secondary antibody.

SDS PAGE AND WESTERN BLOT ANALYSIS

Equal amounts of protein (10 μg) of cell lysates and 50 ng of rHSP70 (StressGen, Victoria, Canada) were electrophoresed on 10% SDS PAGE as described under (5) according to the method of Laemmli (13). Following SDS PAGE the proteins were transferred to Immobilon PVDF membrane (Millipore Corp., Bedford, Mass.) using a standard protocol (14). Non-specific binding of the Immobilon PVDF menbrane was blocked by 5% skim milk in PBS. The blots were incubated for 1 hour each with of the primary HSP72 antibody (Amersham) and the secondary antibody (goat anti-rabbit IgG peroxidase conjugated, BioRad). Immune complexes were detected using the ECL Western blot detection system (Amersham, Braunschweig). For biotinylated samples 20 μl of the samples were subjected to eletrophoresis and transferred to Immobilon PVDF membrane (Millipore Corp., Bedford, Mass.). The membranes were blocked for 1 hour at room temperature in PBS containing 5% blocking reagent (Amersham, NIF833) and 1% Tween-20 (Sigma), washed three times each for 10 minutes in PBS containing 1% Tween-20 (PBS-T) and labeled for 1 hour with horseradish peroxidase-conjugated streptavidin diluted 1:1500 in PBS-T. Biotinylated proteins were detected by-the ECL system.

ANTIBODY BLOCKING EXPERIMENTS

The inhibition assays were performed by preincubation of the target cells with the following antibodies in a final concentration of 5 μg/1×10$^6$ cells for each antibody: RPN1197 (anti-HSP72), an IgG1 isotype-matched control antibody and W6/32 (15). After incubation the cells were washed twice in RPMI1640/10% FCS, and the cytotoxicity test was conducted as described above.

The results obtained for cell line CX2 could be confirmed with human colon carcinoma cell lines HT29. The HT29 cell line is commercially available at the AMERICAN TYPE CULTURE COLLECTION by the number ATCC HTB38. A genotypic characterization may be found in the ATCC catalogue and the literature cited therein.

The accompanying FIGS. 6A to C show the results of the HT29 cell sorting. The experiment was carried out similar to the cell sorting of cell line CX2.

HSP72 is expressed on the surface of the original cell line HT29 on 30 to 40% of the cells. By cell sorting a HT29+ cell line was obtained expressing HSP72 on its surface in 87% of cells, and a HT29– cell line expressing HSP72 in 15% of cells. The HT29 sublines obtained show stable HSP72 expression over at least 20 cell passages as well as an identical pattern of cell surface expression of MHC and cell adhesion molecules.

It becomes clear from these studies that the CX2 cell lines do not constitute a special case but that a generalization to human colon carcinoma cell lines in their entirety will be possible.

Literature
1. Welch, W. J. 1992 Mammalian stress response: cell physiology, structured/function of stres proteins, and implications for medicine and disease. *Physiol. Rev.* 72:1063–1081.
2. Craig, E. A., B. D. Gambill, and R. J. Nelson. 1993. Heat shock proteins: molecular chaperones of protein biogenesis. *Microbiol Rev.* 57:402–414.
3. Welch, W. J., and J. R. Feramisco. 1984. Nuclear and nucleolar localization of the 72,000-dalton heat shock protein in heat-shocked mammalian cells. *J Biol. Chem.* 259:4501–4513.
4. Ferrarini, M., S. Heltai, M. R. Zocchi, and C. Rugarli. 1992. Unusual expression and localization of heat-shock proteins in human tumor cells. *Int. J Cancer* 51:613–619.
5. Multhoff, G., C. Botzler, M. Wiesnet, E. Müller, T. Meier, W. Wilmanns, and R. D. Issels. 1995. A stress-inducible 72-kDa heat-shock protein (HSP72) is expressed on the surface of human tumor cells, but not on normal cells. *Int. J Cancer* 61:272–279.
6. Lamb, J. R., V. Bal, J. B. Rothbard, A. Mehlert, P. Mendez-Samperio, and D. B. Young. 1989. The mycobacterial GroEL stress protein: a comunon target of T-cell recognition in infection and autoimmunity. *J Autoimmun.* 2 Suppl:93–100.
7. Heufelder, A. E., B. E. Wenzel, and R. S. Bahn. 1992. Cell surface localization of a 72 kilodalton heat shock protein in retroocular fibroblasts from patients with Graves' ophthalmopathy. *J Clin. Endocrinol. Metab.* 74:732–736.
8. Jacquier-Sarlin. M. R. K. Fuller, A. T. Dinh-Xuan, M. J. Richard, and B. S. Polla. 1994. Protective effects of hsp70 in inflammation. *Experientia* 50:1031–1038.
9. Polla, B. S., S. Kantengwa, G. J. Gleich, M. Kondo, C. M. Reimert, and A. F. Junod. 1993. Spontaneous heat shock protein synthesis by alveolar macrophages in interstitial lung disease associated with phagocytosis of eosinophils. *Eur. Respir. J* 6:483–488.
10. Ullrich, S. J., E. A. Robinson, L. W. Law, M. Willingham, and E. Appella. 1986. A mouse tumor-specific transplantation antigen is a heat shock-related protein. *Proc. Natl. Acad Sci. U. S. A.* 83:3121–3125.
11. Srivastava, P. K. 1994. Heat shock proteins in immune response to cancer: the Fourth Paradigm. *Experientia* 50:1054–1060.
12. Danscher, G. 1981. Localization of gold in biological tissue. A photochemical method for light and electronmicros-copy. *Histochemistry* 71:81–88.
13. Laemmli, U.K. 1970. Cleavage of structural proteins during the assembly of the head of bacteriophage T4. *Nature* 227:680–685.
14. Towbin, H., T. Staehelin, and J. Gordon. 1979. Electophoretic transfer of proteins from polyacrylamide gels to nitrocellulose sheets: procedure and some applications. *Proc. Natl. Acad. Sci. U.S.A.* 76:4350–4354.
15. Parham, P., M. J. Androlewicz, F. M. Brodsky, N. J. Holmes, and J. P. Ways. 1982. Monoclonal antibodies: purification, fragmentation and application to structural and functional studies of class I MHC antigens. *J Immunol. Methods* 53:133–173.
16. Gomez, F. J., A. M. Gomez, and G. S. J. Deepe. 1992. An 80-Kilodalton antigen from Histoplasma capsulatum that has homology to heat shock protein 70 induces cell-mediated immune responses and protection in mice. *Infect. Immun.* 60:2565–2571.

I claim:

1. Human colon carcinoma cell lines showing a stable expression of HSP72 of >80% or <20% and an essentially identical cell surface protein expression pattern of MHC and cell adhesion molecules.

2. Human colon carcinoma cell line according to claim 1, characterized in that said cell line is a CX2 or HT29 derived cell line.

3. Human colon carcinoma cell line according to claim 1, characterized in that said cell line shows a HSP72 expression of >90% or <10%.

4. Human colon carcinoma cell line CX+ showing a stable HSP72 cell surface expression of >80%, preferably >90% and having accession No. DSM ACC 2287.

5. Human colon carcinoma cell line CX– showing a stable HSP72 cell surface expression of <20%, preferably <10% and having accession No. DSM ACC 2288.

6. Human colon carcinoma cell line according to claim 1, having a uniform cell surface expression pattern of the cell adhesion molecules ICAM, NCAM, and VCAM.

7. A method for the preparation of human colon carcinoma cell lines according to claim 1, characterized in that a human colon carcinoma cell line expressing HSP72 on its surface is separated by cell sorting into two sublines, wherein one of the sublines expresses more than 80% of HSP72 and the other subline expresses less than 20% of HSP72.

8. A method for the preparation of human colon carcinoma cell lines according to claim 5 characterized in that a human colon carcinoma cell line expressing HSP72 on its surface is separated by cell sorting into two sublines, wherein one of the sublines expresses more than 80% of HSP72 and the other subline expresses less than 20% of HSP72.

9. Human colon carcinoma cell line according to claim 2 characterized in that said cell line shows a HSP72 expression of >90% or <10%.

10. Human colon carcinoma cell line according to claim 4 having a uniform cell surface expression pattern of the cell adhesion molecules ICAM, NCAM, and VCAM.

11. Human colon carcinoma cell line according to claim 5 having a uniform cell surface expression pattern of the cell adhesion molecules ICAM, NCAM, and VCAM.

12. A method for the preparation of human colon carcinoma cell lines according to claim 4 characterized in that a human colon carcinoma cell line expressing HSP72 on its surface is separated by cell sorting into two sublines, wherein one of the sublines expresses more than 80% of HSP72 and the other subline expresses less than 20% of HSP72.

* * * * *

UNITED STATES PATENT AND TRADEMARK OFFICE
CERTIFICATE OF CORRECTION

PATENT NO. : 5,932,478
DATED : August 3, 1999
INVENTOR(S) : Gabriele Multhoff

It is certified that error appears in the above-identified patent and that said Letters Patent is hereby corrected as shown below:

Column 1, line 62, delete "as" and insert --has--

Column 3, line 63, delete "splitted" and insert --split--

Column 4, line 30, delete "splitted" and insert --split--

Column 5, line 6, delete "Tautologous" and insert --autologous--
Column 5, line 55, delete "Tautologous" and insert --autologous--
Column 6, line 15, delete "member" and insert --members--
Column 6, line 36, delete "ICLAIM-I" and insert ---ICAM-1--
Column 7, line 41, delete "QKT3" and insert --OKT3--
Column 7, line 43, delete "H5 P72" and insert --HSP72--
Column 9, line 8, delete "men-" and insert --mem--

Signed and Sealed this

Twenty-ninth Day of May, 2001

Attest:

NICHOLAS P. GODICI

Attesting Officer    Acting Director of the United States Patent and Trademark Office